United States Patent [19]
Endico

[11] Patent Number: 5,328,706
[45] Date of Patent: Jul. 12, 1994

[54] FOOD MANUFACTURING PROCESS UTILIZING HYDROGEN PEROXIDE FOR MICROBIAL CONTROL

[76] Inventor: Felix W. Endico, 440 E. 86th St., New York, N.Y. 10028

[21] Appl. No.: 55,526

[22] Filed: Apr. 29, 1993

[51] Int. Cl.⁵ .................. A23L 3/00; G01N 33/00
[52] U.S. Cl. .................. 426/231; 426/335; 426/532
[58] Field of Search .......... 426/231, 335, 532

[56] References Cited

U.S. PATENT DOCUMENTS

| | | | |
|---|---|---|---|
| 349,852 | 9/1886 | Marchand | 426/532 |
| 1,152,066 | 8/1915 | Wolff | 426/532 |
| 1,630,661 | 5/1927 | Jarson | 426/532 |
| 2,776,214 | 1/1957 | Lloyd et al. | 426/335 |
| 2,916,405 | 12/1959 | Evans | 426/335 |
| 3,525,629 | 8/1970 | Kosikowski | 426/335 |
| 3,615,705 | 10/1971 | Kohl | 426/335 |
| 3,728,134 | 4/1973 | Gilmore | 426/335 |

*Primary Examiner*—George Yeung
*Attorney, Agent, or Firm*—Natter & Natter

[57] ABSTRACT

A food manufacturing process for semi-viscous and viscous food products utilizes an aqueous solution of hydrogen peroxide integrated into the processing procedure for reducing microbial activity. The decomposition of the peroxide is regulated by a protein derived enzyme and is monitored to eliminate the presence of peroxide in the finished food product.

7 Claims, 2 Drawing Sheets

FOOD MANUFACTURING PROCESS UTILIZING HYDROGEN PEROXIDE FOR MICROBIAL CONTROL

BACKGROUND OF THE INVENTION

1. Field of the Invention

This invention relates generally to food technology and especially to the application of an oxidatively active chemical agent for reducing bacterial population.

In particular, the food manufacturing process of this invention utilizes peroxide of hydrogen as a bactericide to improve the preservability of foodstuffs.

2. Background Art

The commercial food processing industry generally relies upon additives, such as preservatives, e.g. sodium benzoate or potassium sorbate, for preventing spoilage, retarding rancidity and prolonging shelf-life.

A problem with these and similar additives is that a residue usually remains in the food product. The residue may not exceed government proscribed levels, typically 1/10th of one (0.1%) percent, nevertheless, these additives may impose a health problem to some individuals and may also adversely affect the flavor or taste of the food product for example, by changing the pH balance.

Although chemical processing agents such as hydrogen peroxide, have received approval from the FDA, as being generally recognized as safe (GRAS), the use of these agents have been rather limited. For example, specified applications for food treatment include use as an antimicrobial agent in milk and starch, as an oxidizing and reducing agent in the preparation of dried eggs and wine, as a bleaching agent for preparing instant tea, cheese whey, herring, tripe and beef feet, and in the reduction or removal of sulfur dioxide from corn syrup and wine vinegar.

A specific application of hydrogen peroxide for the treatment of meat is discussed in U.S. Pat. No. 349,852. In accordance with the process disclosed, hydrogen peroxide is introduced under pressure to meat contained within hermetically sealed containers. These processing conditions, however, are impractical for use with current methods of food processing and packaging.

Another process, as described in U.S. Pat. No. 1,630,661, for the destruction of bacteria in milk, relies upon heat for decomposing the hydrogen peroxide. The use of a thermal catalyst may provide an undue limitation upon the applications of the process especially to foods wherein heat would be detrimental to the edible material.

A further application of hydrogen peroxide food treatment is described in U.S. Pat. No. 3,728,134, wherein dehydrated onion pieces are sprayed with an aqueous hydrogen peroxide solution and then dried. This procedure is apparently suited for selected food products and does not appear to present a widely acceptable and cost efficient method such as contemplated in the instant processing system.

Another problem with the above-described bactericidal procedures is that they are not adapted for integration with automatic batch-feed or continuous-feed manufacturing and production techniques employed in the food industry. The previously described procedures are further restricted to specific food products that do not include semi-viscous or highly viscous flowable food products.

BRIEF SUMMARY OF THE INVENTION

The process of this invention provides a solution to the deficiencies posed by the aforementioned hydrogen peroxide sterilization procedures.

Briefly, the methodology of this invention includes the introduction of a selected combination of premixed moisture compensated food constituents within a mixing vessel, adding a metered quantity of an aqueous solution of hydrogen peroxide, introducing a catalytic agent for accelerating the chemical decomposition of the hydrogen peroxide, mechanically agitating the contents within the mixing vessel for oxidatively treating the food constituents and transferring the treated food constituents to a dispensing station for discharge into containers.

The procedure further incorporates a monitoring system for coordinating the oxidation reaction time in correspondence with the food processing sequence.

The monitoring procedure utilizes a sensing device for detecting oxygen as a byproduct of the decomposition of hydrogen peroxide, and for analyzing this information in a microprocessor. The microprocessor generates signals controlling the operation of the discharge from the mixing vessel to eliminate the presence of hydrogen peroxide in the finished food product. In a variant procedure, the microprocessor generates signals for automatically regulating one or more chemical and/or physical variables such as mixing time, food flow rate, hydrogen peroxide dosing rate and catalyst release rate.

Another feature of the manufacturing process is that it is compatible for use with aseptic food packaging.

In view of the foregoing, it should be apparent that the present invention overcomes many of the problems of the prior art and provides a manufacturing process utilizing hydrogen peroxide for antimicrobial action upon a wide range of microorganisms.

Having thus summarized the invention, it will be seen that it is an object thereof to provide a food manufacturing process of the general character described herein which is not subject to the aforementioned shortcomings.

Another object of this invention is to provide a food manufacturing process that does not rely upon chemical preservatives and does not change the pH value of the food product.

A further object of this invention is to provide a food manufacturing process wherein the food constituents are treated with an oxidatively active chemical agent for controlling microbial activity.

A further object of this invention is to provide a food manufacturing process wherein an accelerant is utilized for coordinating the attrition rate of the oxidant with the corresponding food processing sequence.

Another object of this invention is to provide a food manufacturing process having the capabilities of testing for the presence of hydrogen peroxide and for automatically adjusting one or more of the processing variables to eliminate hydrogen peroxide residue in the finished food product.

A still further object of this invention is to provide a food manufacturing process utilizing hydrogen peroxide for preventing bacterial contamination that is adapted for automatic batch-feed and continuous-feed food processing operations.

With these ends in view, the invention finds embodiment in the procedures by which the aforementioned objects and certain other objects are hereinafter attained, all as more fully described with reference to the accompanying drawings and the scope of which is more particularly pointed out and indicated in the appended claims.

BRIEF DESCRIPTION OF THE DRAWINGS

In the accompanying drawings in which are shown exemplary procedures in accordance with the principles of this invention.

DETAILED DESCRIPTION OF THE INVENTION

With specific reference now to the drawings, it is stressed that the particulars shown and described are for the purposes of illustrative discussion of the process of this invention and are presented in the cause of providing what is believed to be the most useful and readily understood description of the principles and conceptual aspects of the process of this invention. In this regard, no attempt is made to show the process in more detail than is necessary for fundamental understanding of the invention, however, the description in combination with the drawings should make apparent to those skilled in the art how the process may be applied in practice.

Figure 1:
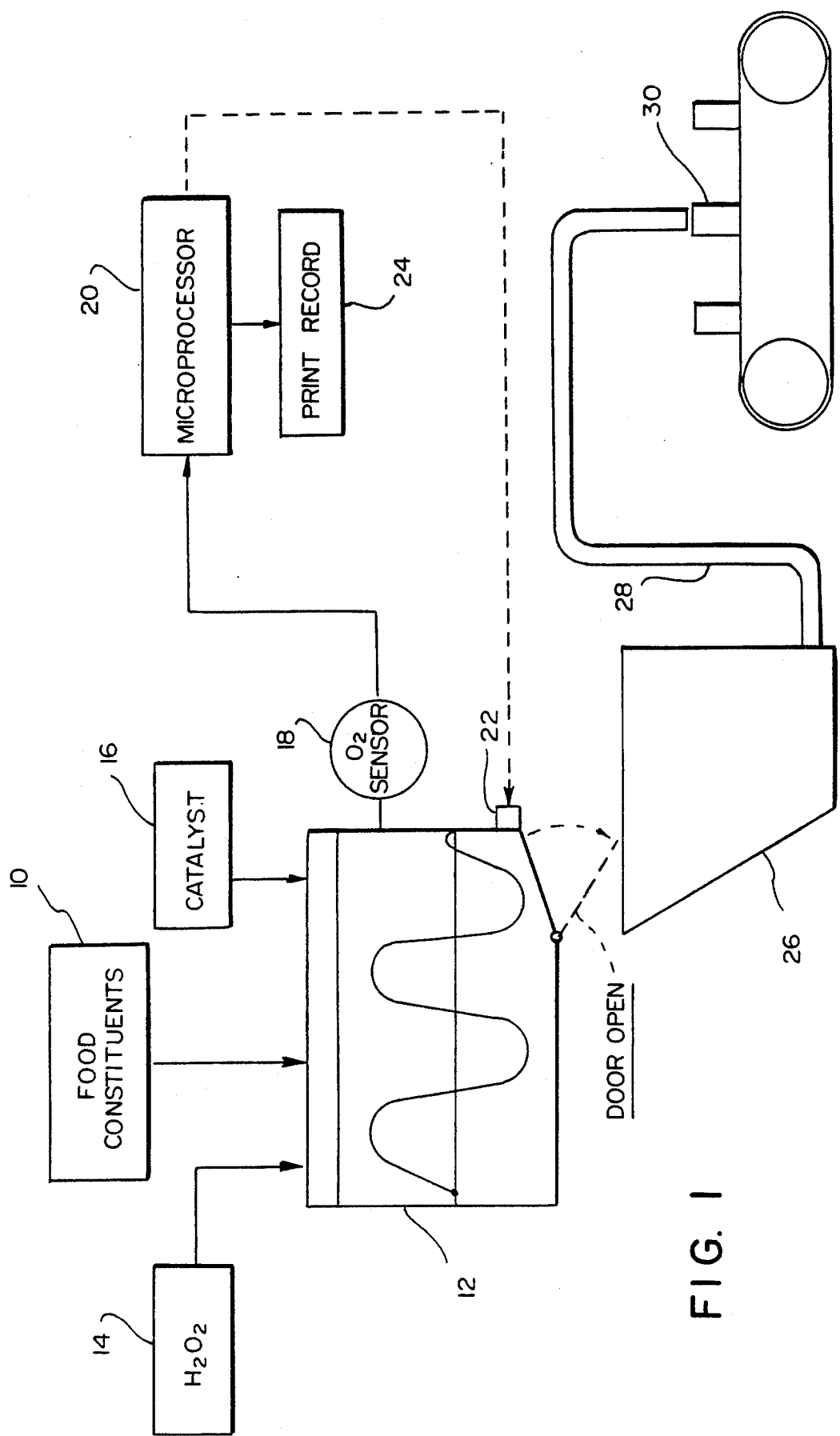
FIG. 1 is a schematic diagram illustrating the food manufacturing process of this invention as applied to a batch-feed operation.

Referring now to FIG. 1, there is shown a batch-feed food manufacturing process in accordance with this invention. The initial stage of the procedure involves the formulation of a combination or premix of food constituents 10 including water, condiments and other ingredients as required for the production of selected foodstuffs, e.g. tuna salad, egg salad, shrimp salad, etc. The food constituents 10 are placed within a stainless steel mixing vessel such as a ribbon blender 12. An oxidatively active compound, such as hydrogen peroxide 14, is metered for calibrated dosing into the ribbon blender 12 wherein it mixes and reacts with the food constituents 10. By way of further explanation, the preferable form of hydrogen peroxide 14 is in a lightly stabilized food-grade liquid state such as available from Interox America, of Houston, Tex.

The interaction of hydrogen peroxide 14 with the food constituents 10 yields clean inert byproducts, namely water and oxygen. The oxygen destroys bacterial growth without changing the pH balance or adversely affecting the food flavor and taste characteristics. It should also be noted that the quantity of water that is added to the food constituents 10 is preadjusted to compensate for the resultant moisture gain upon decomposition of the peroxide 14.

For the purposes of maximizing the effectiveness of the oxidation treatment and for accomplishing complete removal of any residue of the hydrogen peroxide 14 during the food processing procedure, a catalyst 16 is introduced to accelerate the attrition rate. The preferred catalyst 16 is a protein derived enzyme, such as available under the trademark Microcatalase, manufactured by Solvay Enzymes, Inc. of Elkhart, Ind. Microcatalase is a standardized liquid enzyme obtained by controlled fermentation of *Micrococcus lysodeikticus* that specifically catalyzes the decomposition of hydrogen peroxide into water and molecular oxygen.

The processing sequence further includes mixing the food constituents 10, the hydrogen peroxide 14 and the catalyst 16 within the blender 12 for a fixed period of time usually about ten (10) to fifteen (15) minutes, and then holding the contents within the blender 12 until it can be determined that the oxidation treatment has been completed. For this purpose, an oxygen sensor 18 is used for testing for the presence of hydrogen peroxide 14 within the blender 12 as a factor of the liberated oxygen. The sensor 18 is designed to transmit signals to a microprocessor 20. The microprocessor 20 in turn interprets the data and generates a signal to operate a solenoid actuated door release 22 in the blender 12 for discharging the food constituents 10 that have been subjected to the microbial treatment.

It should also be noted that the microprocessor 20 will concurrently transmit data to a chart recorder 24 for providing a print record of the hydrogen peroxide presence during the mixing and unloading stages. The peroxide content can also be detected by analyzing a sample of the food constituents 10 using titration.

The sterilized food constituents 10 are then placed in a hopper 26 and subsequently flowably transported through a pipe network 28 for discharge into a plurality of individual containers 30 that are typically positioned on a conveyor belt. The process is also adaptable for "cold-pack" aseptic food packaging at ambient temperatures. The hydrogen peroxide treatment effectively eliminates the need for aseptic "hot-filling" as is conventionally employed in the food industry.

By way of further example, the hydrogen peroxide 14 is preferably a five (5%) percent solution that is prepared by mixing one (1) volume of thirty-five (35%) percent hydrogen peroxide with six (6) volumes of drinking water. It should be noted that the reaction time for the oxidation treatment can be further controlled by the addition of heat during the mixing phase to accelerate the chemical reaction. Furthermore, the heat generated by the oxidation reaction, which can be detected by a heat sensitive probe, provides a basis for determining the termination of the reaction.

The above described process is intended for use particularly for highly viscous food products including tuna salad, shrimp salad, egg salad, potato salad, meat-pie fillings, etc. A variant form of the food manufacturing process of this invention, particularly adapted for use with semi-viscous flowable food products such as catsup, pickle relish, sauces and salad dressings, is shown in FIG. 2.

Figure 2:
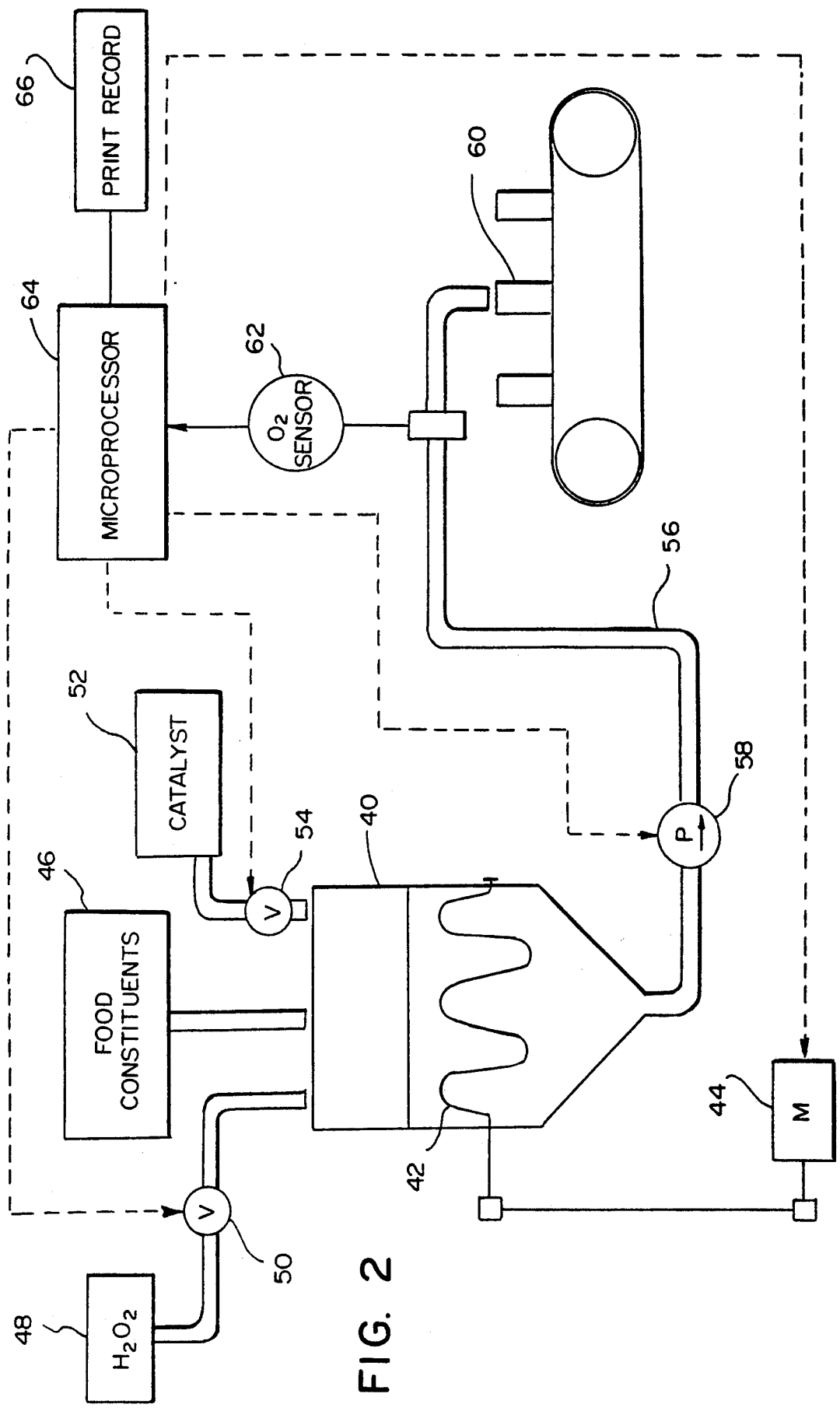
FIG. 2 is a schematic diagram illustrating the food manufacturing process of this invention as applied to an alternate continuous-feed operation.

Referring now to FIG. 2, there is schematically shown a diagram illustrating a continuous-feed food manufacturing procedure utilizing chemical oxidation for microbial control. A stainless steel mixing vessel 40 includes a horizontally mounted agitator 42 that is driven by a motor 44. A calibrated quantity of hydrogen peroxide 48 is added to a selected combination of food constituents 46 placed within the mixing vessel 40. A metering pump 50 is used to control the dosing flow rate of the hydrogen peroxide 48. A catalyst 52 is introduced in selected quantities using an automatic valve control 54. It should be noted that the food constituents 46 can be preadjusted for moisture gain as previously discussed. Additionally, the preferred catalyst 52 is Microcatalase.

The food constituents 46 within the vessel 40 are dispersed by the action of the agitator 42 as operated by the motor drive 44. It is at this mixing stage that the antimicrobial action is initiated. It should be noted that during decomposition of the hydrogen peroxide 48, which is an exothermal reaction, the temperature of the food constituents 46 will be elevated and a compensating factor (e.g. withdrawal of heat energy) can be initiated if the thermal action would be detrimental to the final food product. Conversely, heat may be applied for accelerating the reaction time. Additionally, the temperature differentials can be monitored and used as an indicator of when the reaction has been completed.

The peroxide 48 is continually added to the food constituents 46 within the mixing vessel 40 and the catalyst 52 is also added on a continual basis. At the termination of the mixing phase, the food constituents 46 are flowably transported within a pipe network 56 by the action of a discharge pump 58 and dispensed at a filling station into a plurality of containers 60 in a similar manner as previously described with regard to the batch-feed operation.

Typically, the continuous food process as described herein, from the initiation of the mixing phase until discharge into the containers 60, can be completed in a time frame of approximately ten (10) to fifteen (15) minutes.

The decomposition of the hydrogen peroxide 48 is monitored and the process is controlled so as to remove all presence of hydrogen peroxide 48 when the food is deposited in containers 60. For this purpose, one or more sensors 62 are employed to test for the presence of liberated oxygen within the food transported through the pipe network 56. The information detected by the sensor 62 is transmitted to a microprocessor 64. The microprocessor 64 in turn, generates an output signal to control one or more of the peroxide metering pump 50, the catalyst valve control 54, the discharge pump 58, the agitator motor drive 44. Thus one or more feedback loops are established for regulating either the hydrogen peroxide dosing rate, the catalyst introduction rate, the food discharge flow rate and/or the food mixing rate. The control of one or more of the aforementioned chemical or physical variables can thus be coordinated to adjust the rate of oxidation within the food processing sequence. In addition, the microprocessor 64 transmits data to a chart recorder 66 for providing a print record.

Furthermore, in place of or in conjunction with the sensors 18, 62, a heat probe can be placed in the respective blender 12 or in the mixing vessel 40 for measuring temperature change as a function of the progress of the exothermic reaction. This will provide other basis for indicating when the hydrogen peroxide 14, 48 has been removed from the food constituents 10, 46.

It should thus be seen that there is provided a food manufacturing process utilizing hydrogen peroxide for microbial control which achieves the various objects of this invention and which is well adapted to meet conditions of practical use.

Since possible variations of the process might be made to the exemplary forms set forth, it is to be understood that the process shown and described should be interpreted as illustrative and not in a limiting sense.

Having thus described the invention, there is claimed as new and desired to be secured by Letters Patent:

1. A food manufacturing process for semi-viscous and viscous food products utilizing hydrogen peroxide for microbial control including the steps of:
   (a) preparing a selected combination of food constituents having a moisture component;
   (b) mixing the food constituents for a predetermined duration;
   (c) adding a metered quantity of hydrogen peroxide to the food constituents for oxidatively reacting to remove microorganisms;
   (d) reducing the moisture component of the food constituents in correspondence with the moisture gain upon decomposition of the hydrogen peroxide;
   (e) introducing a catalyst during the processing sequence for accelerating the oxidative reaction time;
   (f) monitoring the hydrogen peroxide attrition rate by sensing the presence of oxygen within the food constituents;
   (g) discharging the processed food constituents after completion of the oxidative reaction; and
   (h) adjusting at least one of the hydrogen peroxide metering rate, the catalyst introduction rate, the food discharge flow rate, the food mixing rate, and the duration of food mixing time by microprocessor control means responsive to the sensed oxygen content wherein the discharged processed food constituents do not contain residual hydrogen peroxide.

2. A food manufacturing process utilizing hydrogen peroxide for microbial control as claimed in claim 1 wherein the duration of the food processing sequence is about 10 to 15 minutes.

3. A food manufacturing process utilizing hydrogen peroxide for microbial control as claimed in claim 1 further including the step of:
   (i) generating a print record of the oxygen content within the food constituents during the food processing sequence by microprocessor control means.

4. A food manufacturing process utilizing hydrogen peroxide for microbial control as claimed in claim 1 further including the step of:
   (i) measuring the temperature differential during mixing of the food constituents for determining when the oxidative reaction has been completed.

5. A food manufacturing process utilizing hydrogen peroxide for microbial control as claimed in claim 1 wherein the catalyst is a protein derived enzyme.

6. A food manufacturing process utilizing hydrogen peroxide for microbial control as claimed in claim 5 wherein the catalyst is Microcatalase.

7. A food manufacturing process utilizing hydrogen peroxide for microbial control as claimed in claim 5 wherein the hydrogen peroxide is in a five (5%) percent aqueous solution.

* * * * *